(12) United States Patent
Ben Hur et al.

(10) Patent No.: US 8,489,531 B2
(45) Date of Patent: *Jul. 16, 2013

(54) IDENTIFICATION OF CO-REGULATION PATTERNS BY UNSUPERVISED CLUSTER ANALYSIS OF GENE EXPRESSION DATA

(75) Inventors: Asa Ben Hur, Seattle, WA (US); Andre Elisseeff, Thalwil (CH); Isabelle Guyon, Berkeley, CA (US)

(73) Assignee: Health Discovery Corporation, Savannah, GA (US)

( * ) Notice: Subject to any disclaimer, the term of this patent is extended or adjusted under 35 U.S.C. 154(b) by 351 days.

This patent is subject to a terminal disclaimer.

(21) Appl. No.: 13/019,585

(22) Filed: Feb. 2, 2011

(65) Prior Publication Data

US 2011/0125683 A1 May 26, 2011

Related U.S. Application Data

(63) Continuation of application No. 11/929,522, filed on Oct. 30, 2007, now Pat. No. 7,890,445, which is a continuation of application No. 10/478,191, filed as application No. PCT/US02/15666 on May 17, 2002, now abandoned.

(60) Provisional application No. 60/335,990, filed on Nov. 30, 2001, provisional application No. 60/292,221, filed on May 18, 2001.

(51) Int. Cl.
*G06F 17/00* (2006.01)
*G06N 5/00* (2006.01)

(52) U.S. Cl.
USPC .............................. 706/45; 800/294; 435/193

(58) Field of Classification Search
USPC ........................................... 800/294; 435/193
See application file for complete search history.

(56) References Cited

U.S. PATENT DOCUMENTS

| | | | |
|---|---|---|---|
| 5,572,628 A | 11/1996 | Denker et al. | |
| 5,649,068 A | 7/1997 | Boser et al. | |
| 5,950,146 A | 9/1999 | Vapnik | |
| 6,128,608 A | 10/2000 | Barnhill | |
| 6,157,921 A | 12/2000 | Barnhill | |
| 6,263,287 B1 * | 7/2001 | Zheng et al. | 702/20 |

(Continued)

OTHER PUBLICATIONS

Mariadason et al. Genetic reprogramming in pathways of colonic cell maturation induced by short chain fatty acids: Comparison with Trichostatin A, Sulindac, Curcumin and implications for chemoprevention of colon cancer. Cancer Research, vol. 60, Aug. 15, 2000, pp. 4561-4572.

(Continued)

*Primary Examiner* — Kakali Chaki
*Assistant Examiner* — Kalpana Bharadwaj
(74) *Attorney, Agent, or Firm* — Eleanor M. Musick; Procopio, Cory, Hargreaves & Savitch, LLP

(57) ABSTRACT

A method is provided for unsupervised clustering of gene expression data to identify co-regulation patterns. A clustering algorithm randomly divides the data into k different subsets and measures the similarity between pairs of datapoints within the subsets, assigning a score to the pairs based on similarity, with the greatest similarity giving the highest correlation score. A distribution of the scores is plotted for each k. The highest value of k that has a distribution that remains concentrated near the highest correlation score corresponds to the number of co-regulation patterns.

24 Claims, 13 Drawing Sheets

U.S. PATENT DOCUMENTS

| | | | |
|---|---|---|---|
| 6,267,722 | B1 | 7/2001 | Anderson et al. |
| 6,427,141 | B1 | 7/2002 | Barnhill |
| 6,658,395 | B1 | 12/2003 | Barnhill |
| 6,714,925 | B1 | 3/2004 | Barnhill et al. |
| 6,760,715 | B1 | 7/2004 | Barnhill et al. |
| 6,789,069 | B1 | 9/2004 | Barnhill et al. |
| 6,882,990 | B1 | 4/2005 | Barnhill et al. |
| 6,944,602 | B2 | 9/2005 | Cristianini |
| 2002/0049543 | A1* | 4/2002 | Nakashige et al. ............ 702/19 |
| 2003/0074369 | A1 | 4/2003 | Schuetze et al. |

OTHER PUBLICATIONS

Golub et al. Molecular classification of cancer: class discovery and class prediction by gene expression monitoring. Science, vol. 286, 1999, pp. 531-537.

Ben-Dor, et al., "Clustering Gene Expression Patterns", Journal of Computational Biology, Fall-Winter, 1999, pp. 281-297, vol. 6, Issue 3-4.

Bradley, et al., "Refining Initial Points for K-Means Clustering", Proceedings of the 15th International Conference on Machine Learning (ICML98), Edited by J. Shavlik, 1998, pp. 91-99, Morgan Kaufmann, San Francisco.

Dettling, et al., "Supervised Clustering of Genes", Genome Biology, 2002, 3(12): research0069.1-0069.15.

Dubnov, et al., "A New Nonparametric Pairwise Clustering Algorithm Based on Iterative Estimation of Distance Profiles", Machine Learning, 2002, pp. 35-61, vol. 47, Kluwer Academic Publishers, Manufactured in The Netherlands.

Eisen, et al., "Cluster Analysis and Display of Genome-wide Expression Patterns", Proceedings of the National Academy of Sciences, Genetics, Dec. 1998, pp. 14863-14868, vol. 95.

Hastie, et al., "Estimating the Number Of Data Clusters Via the Gap Statistic", Journal of the Royal Statistical Society: Series B, 2001, pp. 411-423, vol. 63.

Hilsenbeck, et al., "Statistical Analysis of Array Expression Data as Applied to the Problem of Tamoxifen Resistance", Journal of the National Cancer Institute, Mar. 3, 1999, pp. 453-459, vol. 91, No. 5.

Levine, et al., "Resampling Method for Unsupervised Estimation of Cluster Validity", Neural Computation, Nov. 2001, pp. 2573-2593, vol. 13, Issue 11.

Meilă, "Data Centering in Feature Space", 9th International Workshop on Artificial Intelligence and Statistics, Jan. 2003.

Michaels, et al., "Cluster Analysis and Data Visualization of Large-scale Gene Expression Data", Pacific Symposium on Biocomputing, 1998, pp. 42-53, vol. 3.

Schölkopf, et al., "Incorporating Invariances in Support Vector Learning Machines", Proceedings of the 1996 International Conference on Artificial Neural Networks, Lecture Notes in Computer Science, 1996, pp. 47-52, vol. 1112, Springer, Berlin.

* cited by examiner

IDENTIFICATION OF CO-REGULATION PATTERNS BY UNSUPERVISED CLUSTER ANALYSIS OF GENE EXPRESSION DATA

RELATED APPLICATIONS

This application is a continuation of application Ser. No. 11/929,522, filed Oct. 30, 2007, issued Feb. 15, 2011 as U.S. Pat. No. 7,890,445, which is a continuation of application Ser. No. 10/478,191, filed Nov. 18, 2003, now abandoned, which is a U.S. National Stage filing of PCT/US02/15666, filed May 17, 2002, which claims the benefit of U.S. provisional patent applications No. 60/335,990, filed Nov. 30, 2001, and No. 60/292,221, filed May 18, 2001. Each of the identified applications is incorporated herein by reference.

FIELD OF THE INVENTION

The present invention relates to the use of learning machines to identify relevant patterns in datasets containing large quantities of diverse data, and more particularly to a method and system for unsupervised learning for determining an optimal number of data clusters into which data can be divided to best enable identification of relevant patterns.

BACKGROUND OF THE INVENTION

Knowledge discovery is the most desirable end product of data collection. Recent advancements in database technology have lead to an explosive growth in systems and methods for generating, collecting and storing vast amounts of data. While database technology enables efficient collection and storage of large data sets, the challenge of facilitating human comprehension of the information in this data is growing ever more difficult. With many existing techniques the problem has become unapproachable. Thus, there remains a need for a new generation of automated knowledge discovery tools.

As a specific example, the Human Genome Project has completed sequencing of the human genome. The complete sequence contains a staggering amount of data, with approximately 31,500 genes in the whole genome. The amount of data relevant to the genome must then be multiplied when considering comparative and other analyses that are needed in order to make use of the sequence data. As an illustration, human chromosome 20 alone comprises nearly 60 million base pairs. Several disease-causing genes have been mapped to chromosome 20 including various autoimmune diseases, certain neurological diseases, type 2 diabetes, several forms of cancer, and more, such that considerable information can be associated with this sequence alone.

One of the more recent advances in determining the functioning parameters of biological systems is the analysis of correlation of genomic information with protein functioning to elucidate the relationship between gene expression, protein function and interaction, and disease states or progression. Proteomics is the study of the group of proteins encoded and regulated by a genome. Genomic activation or expression does not always mean direct changes in protein production levels or activity. Alternative processing of mRNA or post-transcriptional or post-translational regulatory mechanisms may cause the activity of one gene to result in multiple proteins, all of which are slightly different with different migration patterns and biological activities. The human proteome is believed to be 50 to 100 times larger than the human genome. Currently, there are no methods, systems or devices for adequately analyzing the data generated by such biological investigations into the genome and proteome.

Clustering is a widely used approach for exploratory data analysis. Clustering analysis is unsupervised learning—it is done without suggestion from an external supervisor; classes and training examples are not given a priori. The objective of clustering is to group data points into "meaningful" subsets. There is no agreed upon definition of the clustering problem, and various definitions appear in the literature. For example, clustering has been defined as a search for some "natural" or "inherent" grouping of the data. However, most clustering algorithms do not address this problem. The vast majority of clustering algorithms produce as their output either a dendogram or a partition into a number of clusters, where the number of clusters is either the input, or there is some other parameter(s) that controls the number of clusters. In either case, a model selection technique is required in order to choose the model parameter, or in the case of hierarchical algorithms, to determine which level of the dendogram represents the "inherent" structure of the data.

A few examples of applications of clustering include (1) analysis of microarray data, where co-expressed genes are found, and the assumption is that co-expression might be a sign of co-regulation; (2) in medical datasets (gene expression data, clinical data etc.), where patients are divided into categories; (3) in any set or set of measurements to detect trends or artifacts in the measurement protocol; and (4) in information retrieval to partition text according to categories.

Most clustering algorithms either produce a hierarchical partitioning of the data into smaller and smaller clusters, or produces a partition of a dataset into a number of clusters that depend on some input parameter (the number of clusters or some other parameter(s)). The question remains, however, of how to set the input parameter, or how to determine which level of the tree representation of the data to look at: Clustering algorithms are unsophisticated in that they provide no insight into the level of granularity at which the "meaningful" clusters might be found. Occasionally, there may be prior knowledge about the domain that facilitates making such a choice. However, even in such cases, a method for determining the granularity at which to look at the data is required. This is seen as the problem of finding the optimal number of clusters in the data, relative to some clustering algorithm.

E. Levine and E. Domany in "Resampling Method for Unsupervised Estimation of Cluster Validity", *Neural Comp.* 13, 2573-2593 (2001), assign a figure of merit to a clustering solution according to its similarity to clusterings of sub-samples of the data. The "temperature" parameter of their clustering algorithm is selected according to a maximum of the similarity measure. However, in real data, such a maximum does not often occur. Other model selection techniques have difficulty detecting the absence of structure in the data, i.e., that there is a single cluster. Further, many of algorithms make assumptions as to cluster shape, and do not perform well on real data, where the cluster shape is generally not known. Accordingly, other methods for clustering are needed. The present invention is directed to such a method.

SUMMARY OF THE INVENTION

In an exemplary embodiment, a system and method are provided for analysis of data by grouping the input data points into meaningful subsets of data. The exemplary system comprises a storage device for storing at least one data set, and a processor for executing the clustering algorithm. In the preferred embodiments, the clustering algorithm is a k-means or hierarchical clustering algorithm.

In the method of the present invention, a "good granularity level", i.e., an optimal number of clusters, is defined as one at which a clustering solution is stable with respect to some perturbation of the data, such as noise or sub-sampling. For each level of granularity, the algorithm chooses a number of pairs of sub-samples or other perturbations, clusters each sub-sample with the chosen level of granularity, then computes a similarity between pairs of clustering solutions. For each level of granularity, the distribution of the similarity between pairs of clustering solutions is computed, then the highest level of granularity for which highly similar solutions are obtained under perturbation is chosen.

According to the present invention, the probability distribution of the similarity measure is evaluated in order to find the "true" number of clusters based on a similarity measure between clustering solutions. A dot product between pairs of clustering solutions is normalized to provide a similarity measure. Other similarity measures proposed in the literature can also be expressed in terms of this dot product.

In one embodiment, the inventive method provides means for extraction of information from gene expression profiles, in particular, extraction of the most relevant clusters of temporal expression profiles from tens of thousands of measured profiles. In one variation of the present embodiment, the clustering algorithm is the k-means algorithm. Other embodiments include all pairwise clustering methods (e.g., hierarchical clustering) and support vector clustering (i.e., a support vector machine (SVM)). In one variation, the fit involves affine transformations such as translation, rotation, and scale. Other transformations could be included, such as elastic transformations. In the case of k-means, the algorithm is applied in a hierarchical manner by sub-sampling the data and clustering the sub-samples. The resulting cluster centers for all the runs are then clustered again. The resulting cluster centers are considered to be the most significant profiles. To facilitate the clustering task, a ranking of the genes is first performed according to a given quality criterion combining saliency (significant difference in expression in the profile), smoothness, and reliability (low noise level). Other criteria for ranking include the local density of examples.

DETAILED DESCRIPTION OF THE PREFERRED EMBODIMENTS

Figure 1A:
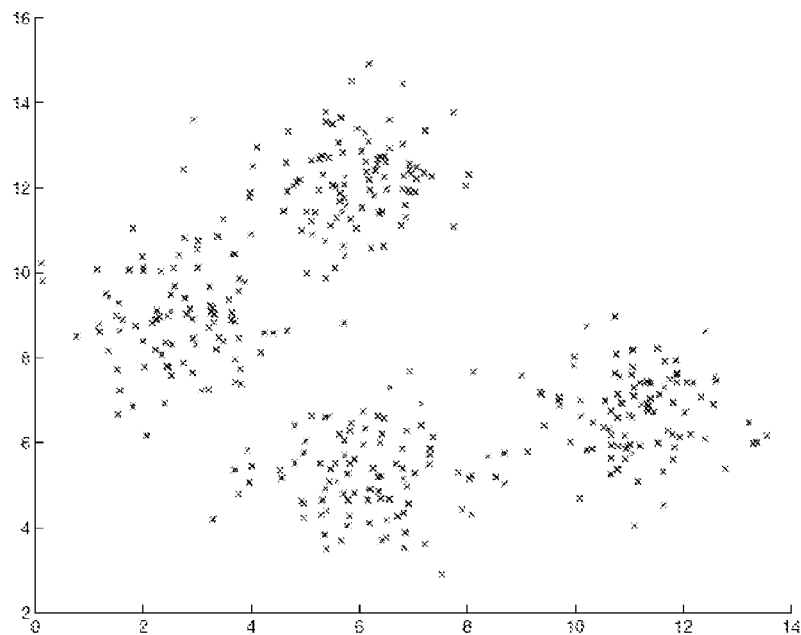
FIGS. 1a-1c are a plot of data which is a mixture of four Gaussians, a histogram of the correlation score for the Gaussian data mixture, and a plot showing the overlay of cumulative distributions of the correlation score, respectively.

A typical computer system for running the inventive clustering algorithm is a Pentium®-class processor with an interface for inputting the dataset(s) of interest and a memory for storing the dataset. Alternative processors include configurable logic processors made up of SRAM-based field programmable gate arrays (FPGAs) or configurable system on chip (CSOC) architectures, which include a processor and an array of configurable logic cells on a single chip, either of which can be used to accelerate computer-intensive operations such as clustering algorithms on large datasets. In addition, parallel implementations in multi-computers have been used for executing clustering algorithms for extracting knowledge from large-scale data repositories. Selection of an appropriate computer system for executing the inventive clustering method is within the level of skill in the art.

The clustering model selection algorithm works with the help of a scoring function that provides a similarity measure between two labelings.

Let $X=\{x_1, \ldots, x_n\}$, and $x_i \in \mathbb{R}^d$ be the dataset to be clustered. A labeling L is a partition of X into k subsets $S_1, \ldots, S_k$. It can be represented by a function $c: X \to \{1, \ldots, k\}$ where $c(x_i)$ is the cluster to which $x_i$ belongs.

A less compact representation of a labeling, which may be useful is the following representation by a matrix C with components:

$$C_{ij} = \begin{cases} 1 & \text{if } x_i \text{ and } x_j \text{ belong to the same cluster,} \\ 0 & \text{otherwise} \end{cases} \quad (1)$$

Note that this representation is label independent, i.e. there is no need to assign each point a label in $\{1, \ldots, k\}$. This may be viewed as an adjacency matrix, where each cluster is a connected component of the graph. This representation can also be converted into a representation of soft cluster labeling.

Let labelings $L_1$ and $L_2$ have matrix representations $C^{(1)}$ and $C^{(2)}$ respectively, so that $$\langle \mathcal{L}_1, \mathcal{L}_2 \rangle = \sum_{i,j} C_{ij}^{(1)} C_{ij}^{(2)} \quad (2)$$

This dot product computes the number of pairs of vectors clustered together, and can also be interpreted as the number of common edges in graphs represented by $C^{(1)}$ and $C^{(2)}$. A naïve method for computing the dot product by going over all pairs of points has complexity $O(n^2)$. However, it can be computed in linear time.

As a dot product, $\langle L_1, L_2 \rangle$ satisfies the Cauchy-Schwartz inequality: $\langle L_1, L_2 \rangle \leq \sqrt{\langle L_1, L_1 \rangle \langle L_2, L_2 \rangle}$. The correlation score, which is a normalized version of the dot product, is:

$$cor(\mathcal{L}_1, \mathcal{L}_2) = \frac{\langle \mathcal{L}_1, \mathcal{L}_2 \rangle}{\sqrt{\langle \mathcal{L}_1, \mathcal{L}_1 \rangle \langle \mathcal{L}_2, \mathcal{L}_2 \rangle}} \quad (3)$$

A. K. Jain and R. C. Dubes, *Algorithms for clustering data* (Prentice Hall, Englewood Cliffs, N.J., 1988) provide a number of scores for comparing a labeling produced by a clustering algorithm with a "gold standard" labeling. This technique is known as "external" validation. In contrast, the present invention proposes the use of scoring functions for "internal" validation that do not require the "gold standard". In the following, it is shown that two commonly used scoring functions can be expressed in terms of the dot product defined above in Equation 2. Given two matrices $C^{(1)}$, $C^{(2)}$ with 0-1 entries, let $N_{ij}$ $i,j \in \{0, 1\}$ be the number of entries on which $C^{(1)}$ and $C^{(2)}$ have values i and j, respectively. Define the matching coefficient as the fraction of entries on which the two matrices agree:

$$M(\mathcal{L}_1, \mathcal{L}_2) = \frac{N_{00} + N_{11}}{N_{00} + N_{01} + N_{10} + N_{11}}. \quad (4)$$

The Jaccard coefficient is the corresponding ratio when "negative" matches are ignored:

$$J(\mathcal{L}_1, \mathcal{L}_2) = \frac{N_{11}}{N_{01} + N_{10} + N_{11}}. \quad (5)$$

The Jaccard coefficient is more appropriate when the clusters are relatively small, since in that case, the $N_{00}$ term will be the dominant factor even if the solution is far from the true one. These scores can be expressed in terms of the labeling dot product and the associated norm according to the following proposition:

Let $C^{(1)}$ and $C^{(2)}$ be the matrix representations of labelings $L_1$ and $L_2$, respectively. Then:

$$J(\mathcal{L}_1, \mathcal{L}_2) = \frac{\langle C^{(1)}, C^{(2)} \rangle}{\langle C^{(1)}, C^{(1)} \rangle + \langle C^{(2)}, C^{(2)} \rangle - \langle C^{(1)}, C^{(2)} \rangle} \quad (6)$$

$$M(\mathcal{L}_1, \mathcal{L}_2) = 1 - \frac{1}{n^2}\|C^{(1)} - C^{(2)}\|^2$$

This is a result of the observation that $N_{11} = \langle C^{(1)}, C^{(2)} \rangle$, $N_{01} = \langle 1_n - C^{(1)}, C^{(2)} \rangle$, $N_{10} = \langle C^{(1)}, 1_n - C^{(2)} \rangle$, $N_{00} = \langle 1_n - C^{(1)}, 1_n - C^{(2)} \rangle$, where $1_n$ is an n×n matrix with entries equal to 1. The above expression for the Jaccard coefficient shows that it is close to the correlation score.

The following list provides the routine for the model explorer algorithm according to the present invention:

```
Input: A dataset D, k_min, k_max
Require: A clustering algorithm, cluster (D, k)
  A scoring function for label comparison, s(L_1, L_2)
  f = 0.8
  for k = k_min to k_max do
    for i = 1 to maximum iterations do
      sub_1 = subsamp(D,f) {a sub-sample with fraction f of the data}
      sub_2 = subsamp(D,f)
      L_1 = cluster (sub_1 , k)
      L_2 = cluster (sub_2 , k)
      Intersect = sub_1 ∩ sub_2
      Score (i, k) = s(L_1(Intersect), L_2(Intersect)){Compute the score
         on the intersection of the two labels}
    end for
  end for
```

When one looks at a cloud of data points, and at a subsample of it for a sampling ratio, f (fraction of points sampled) is not much smaller than 1 (say f>0.5), one usually observes the same general structure. Thus, it is also reasonable to postulate that a clustering algorithm has captured the inherent structure in a dataset if clustering solutions over different subsamples are similar, e.g., according to one of the similarity measures introduced in the previous section. Thus, "inherent structure" is defined as structure that is stable under subsampling (or alternatively, perturbing the data). Given a clustering algorithm and a dataset, this translates into a search for the best number of clusters to use in the particular instance. Note that one can also extend the search to look for a set of features where structure is apparent, however, in this case, the same set of features is kept.

The inventive clustering algorithm receives as input a dataset (or similarity/dissimilarity matrix) and a parameter k that controls either directly or indirectly the number of clusters that the algorithm produces. This convention is applicable to hierarchical clustering algorithms as well: given k, the tree is cut so that k clusters are produced. Next, characterize the stability of the clustering for each k. This is accomplished by producing a set of clusterings of sub-samples of the data, and comparing the labels of the intersection of pairs of clusterings using, for example, the correlation similarity measure. This is performed for increasing values of k (see above for details). The distribution of the scores for the different values of k is then compared (see, e.g., FIGS. 1a-1c). The idea is that when there is structure in the data that is well described by the clustering algorithm with that particular value of k, many sub-samples will produce similar clusterings, and their pairwise similarity score will be concentrated close to 1.

Each sub-sample contains a fixed fraction of the data, f. The actual subsampling can be implemented in various ways:
1. Select each sample independently so that the size of the intersection between two samples is random.
2. Select together pairs of samples by first selecting their intersection, then selecting the rest of the data to complete the fraction f.
3. Fix one clustering solution to be one produced on the whole dataset. (This third option was used by Levine and Domany (supra) to give a figure of merit to a particular clustering solution.)

For k=1, all clusterings are the same. This also holds for k=n, where n is the number of data points; in this case every point is in a different cluster. When the number of clusters becomes large so that there is a small number of points in each cluster, the solution becomes stable. The value of f should not be too low so that there not all clusters are represented in a sub-sample. In the Examples provided below, the shape of the distribution did not depend very much on the specific value of f. Any value between 0.6 and 0.9 worked well.

EXAMPLES

In this section experiments on artificial and real data are described. In all the experiments the distribution of the correlation score is shown. Equivalent results were obtained using other scores as well. The parameter values f=0.8 and 200 pairs of solutions were compared for each k. A hierarchical clustering algorithm was used, with the Ward criterion for merging clusters (see, e.g., Jain and Dubes, supra). Similar results were obtained using other hierarchical clustering methods (complete and average linkage). The advantage of using hierarchical clustering methods is that the same set of clusterings can be used for all values of k.

Example 1

Gaussian Data

Figure 1B:
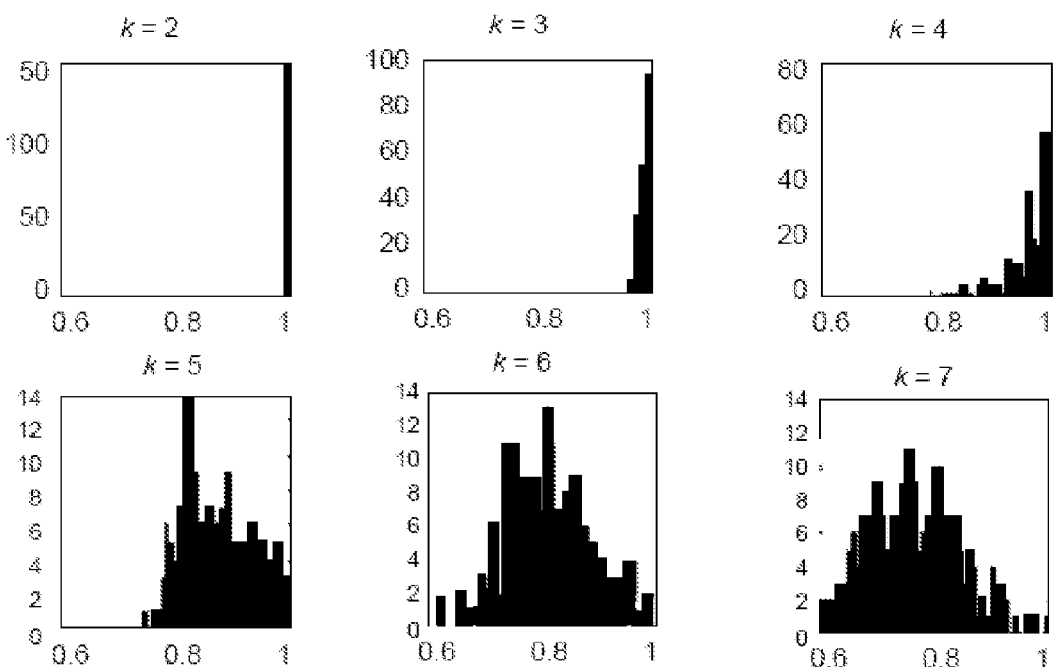
Figure 1C:
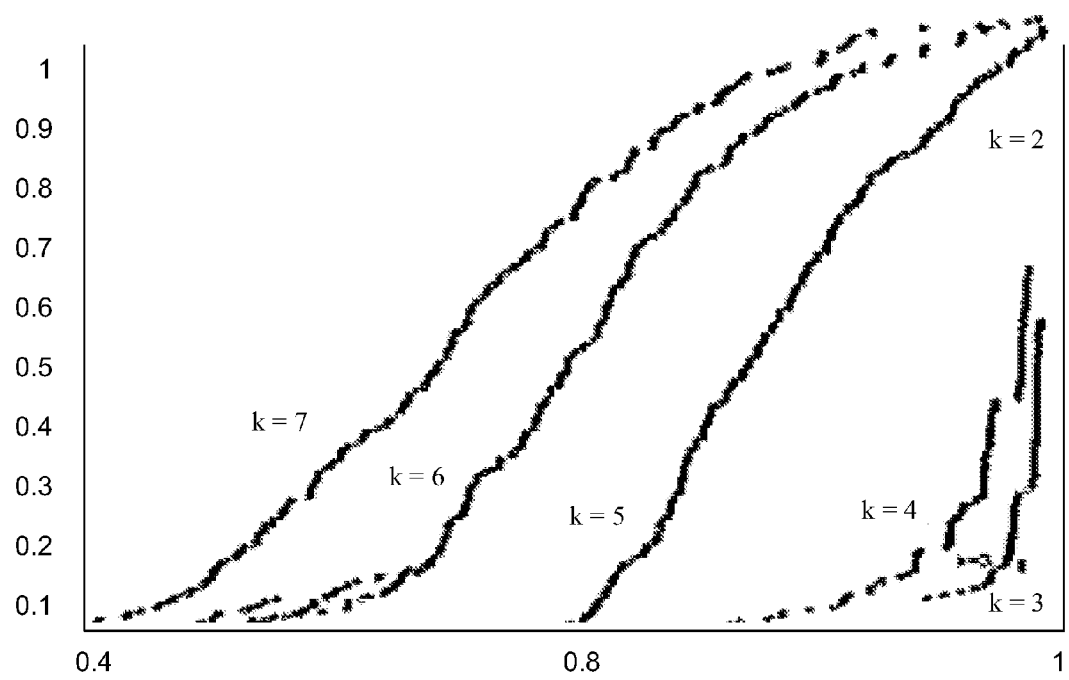

Referring first to FIGS. 1a-1c, FIG. 1a shows a mixture of four Gaussians. The histograms of the score for varying values of k for this data is plotted in FIG. 1b. Histograms are shown for each value of k in the range of 2 to 7. Observations regarding the histograms are that at k=2, there is a peak at 1, since almost all the runs discriminated between the two upper and two lower clusters. At k=3, most runs separated the two lower clusters, and at k=4 most runs found the "correct" clustering as is reflected in the distribution of scores that is still close to 1.0. At k>4 there is no longer essentially one preferred solution. There is, in fact, a wide variety of solutions, evidenced by the widening spectrum of the similarities. FIG. 1c plots the cumulative distributions of the correlation score for each k, where k=2 at the rightmost side of the plot (at peak 1), and k=7 being the leftmost curve.

Example 2

DNA Microarray Data

Figure 2A:
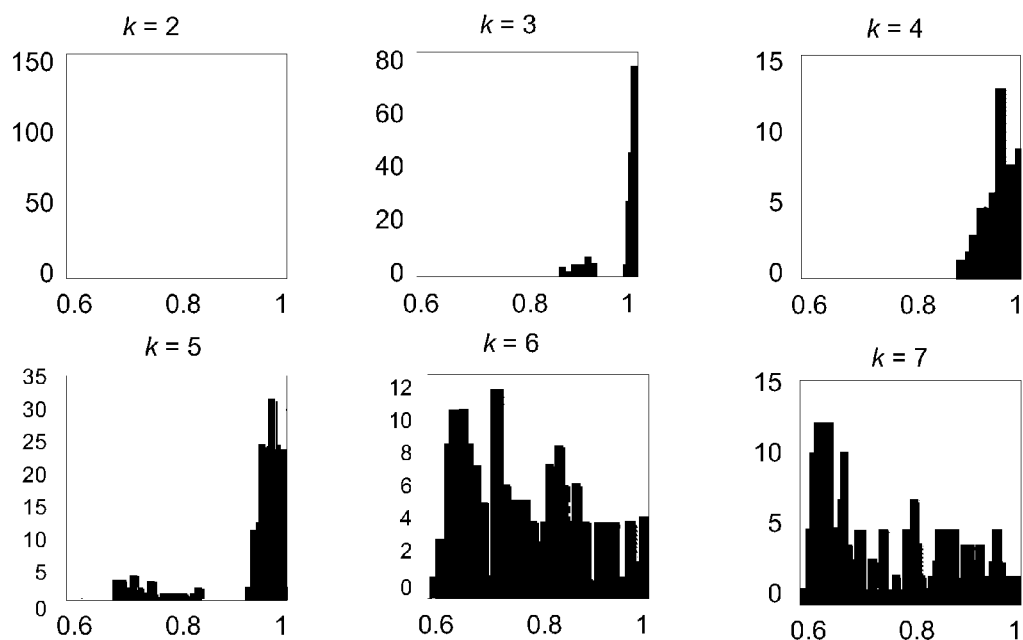
FIGS. 2a and 2b are histogram of the correlation score for the yeast gene expression data and an overlay of the cumulative distributions of the correlation score, respectively.

The next dataset considered was the yeast DNA microarray data of M. Eisen et. al. ("Genetics cluster analysis and display of genome-wide expression patterns", *Proc. Natl. Acad. Sci. USA*, 95: 14863-14868, December 1998.). The data is a matrix which represents the mRNA expression levels of n genes across a number of experiments. Some of the genes in the data have known labels according to a functional class. Five functional classes were selected along with genes that belong uniquely to these five functional classes. This yielded a dataset with 208 genes, with 79 features (experiments). Data was normalized by subtracting the mean and dividing by the standard deviation for each column. This was also performed for the rows, and repeated for the columns. At this stage the first three principal components were extracted. The distribution and histogram of scores is given in FIG. 2a for k over the range of 2 to 7. The same behavior is observed as seen in the mixture of four Gaussians data of FIG. 1a. Between k=5 and k=6, there is a transition from a distribution that has a large component near 1, to a wide distribution that is very similar to the distribution on the random data. The clustering solution that was obtained for k=5 agreed well with the given labels, with a correlation score of 0.95.

Example 3

Uniformly Distributed Data

Figure 3A:
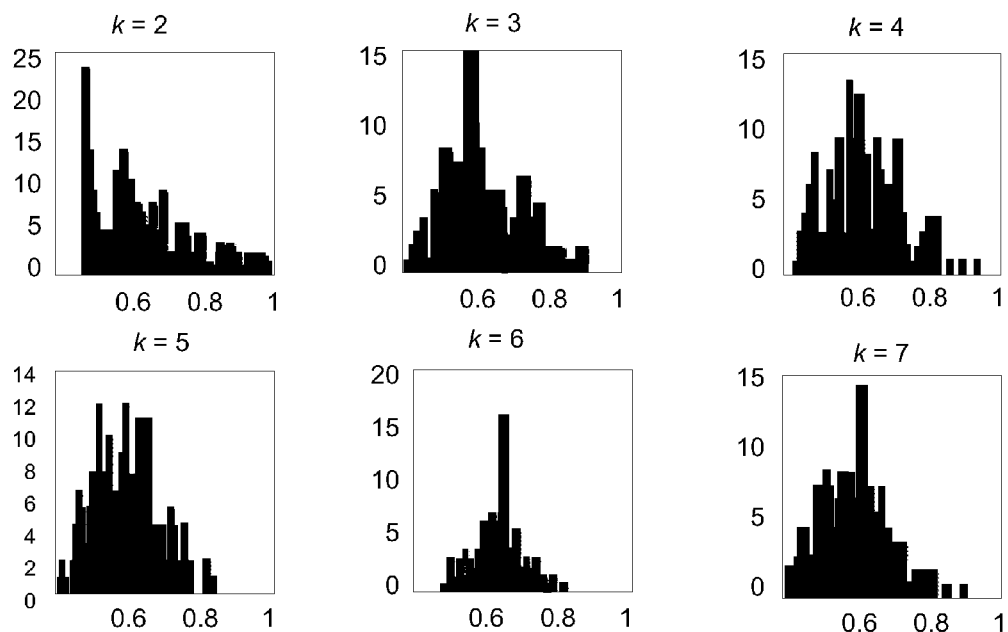
FIGS. 3a and 3b are a histogram of the correlation score for 208 points uniformly distributed on the unit cube and an overlay of the cumulative distributions of the correlation score, respectively.
Figure 3B:
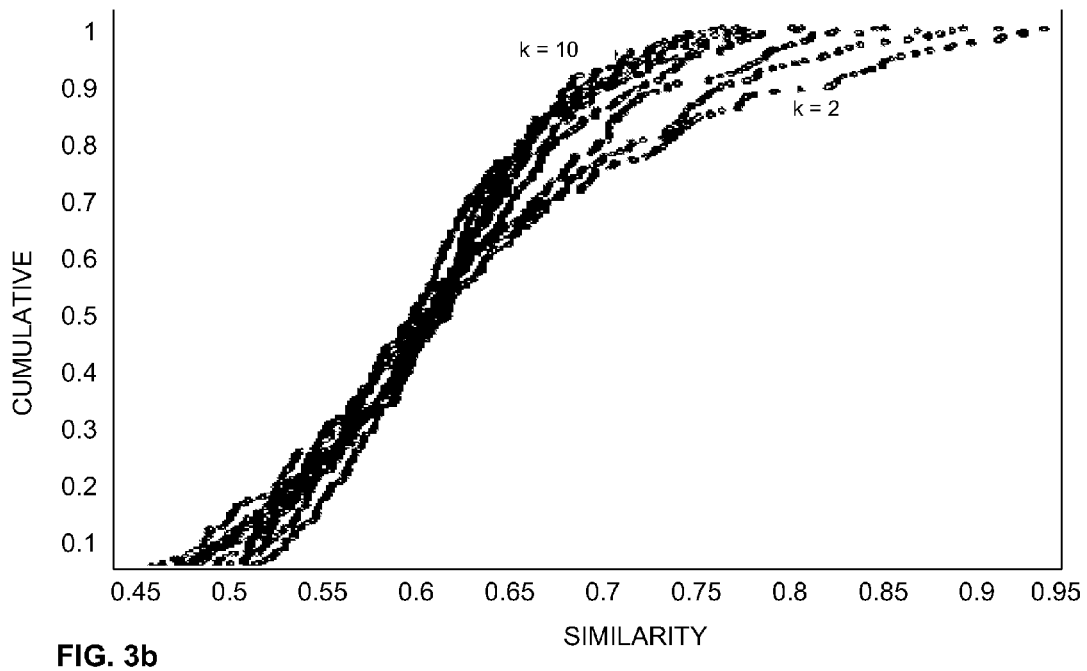

The results of a test run on data uniformly distributed on the unit cube is shown in FIGS. 3a and 3b. The distributions are quite similar to each other, with no change that can be interpreted as a transformation from a stable set of solutions to unstable solutions The preceding examples indicate a simple way for choosing k as the value where there is a transition from a score distribution that is concentrated near 1 to a wider distribution. This can be quantified, e.g., by an increase in the area under the cumulative distribution function or by an increase in $S(K)=P(s>0.90)$.

The value of 0.9 is arbitrary, but any value close to 1 would work on the set of examples considered here.

Example 4

Isolet Letter Pronunciation

The next test was run on a portion of the ISOLET (Isolated Letter Speech Recognition) database created by Ron Cole and Mark Fanty of the Department of Computer Science and Engineering, Oregon Graduate Institute, Beaverton, Oreg. and available from the UCI (University of California at Irvine) Repository of Machine Learning Databases. (This data set was generated by having 150 subjects speak the name of each letter of the alphabet twice, generating 52 training examples from each speaker.) This test provides an example of what occurs with there is cluster overlap.

Figure 4A:
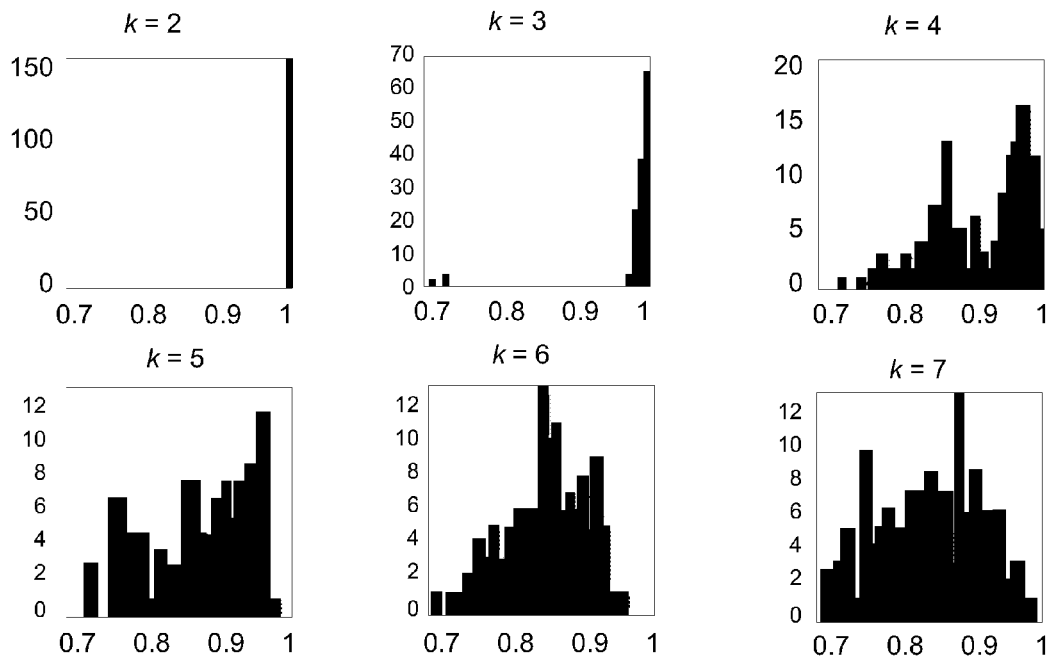
FIGS. 4a-4c are a plot of the first two principle components, the histogram of the correlation score, and an overlay of the cumulative distributions of the correlation score; k=2 (rightmost) to k=10 (leftmost), respectively.
Figure 4B:
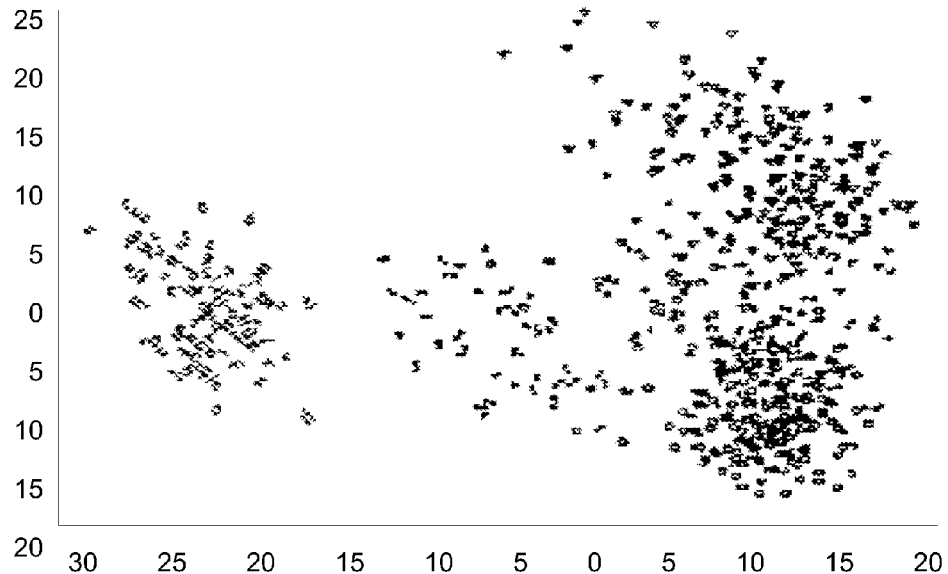
Figure 4C:
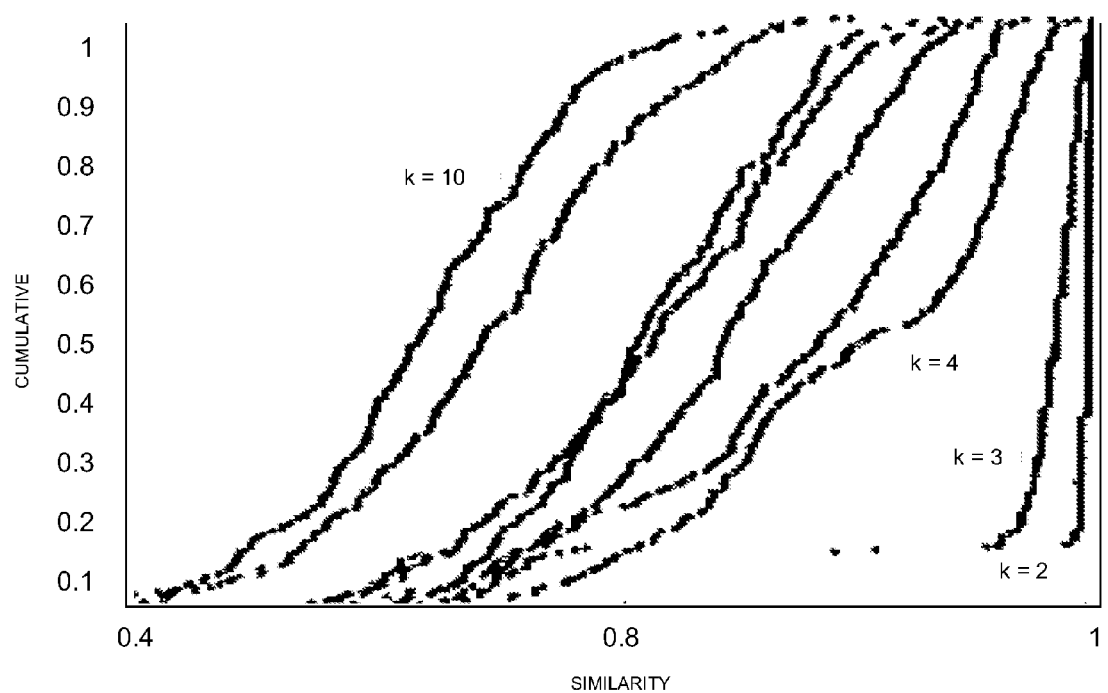

One thousand points of the original dataset, representing the letters "a", "c", "d", "e", "f" were used. The columns of the data were "whitened", then the first three principle components were extracted. FIG. 4a is a plot of the distribution of the first two principle components for each of the selected letters. FIG. 4b provides histograms of the correlation score for each k in the range of 2 to 7, and FIG. 4c is an overlay of the cumulative distribution of the correlation score with k=2 towards the far right side of the plot (near 1) and k=10 towards the left hand side of the plot.

Table 1 provides a comparison of the number of clusters identified using the inventive method against the number of clusters obtained using other methods for selecting k. These other methods are described by R. Tibshirani, G. Walther, and T. Hastie in "Estimating the number of clusters in a dataset via the Gap statistic", *Tech. Report, Department of Statistics, Stanford University*, 2000; also published in *JRSSB* 2000, where the Gap Statistic methods is shown to be superior to a number of other methods.

TABLE 1

Figure 2B:
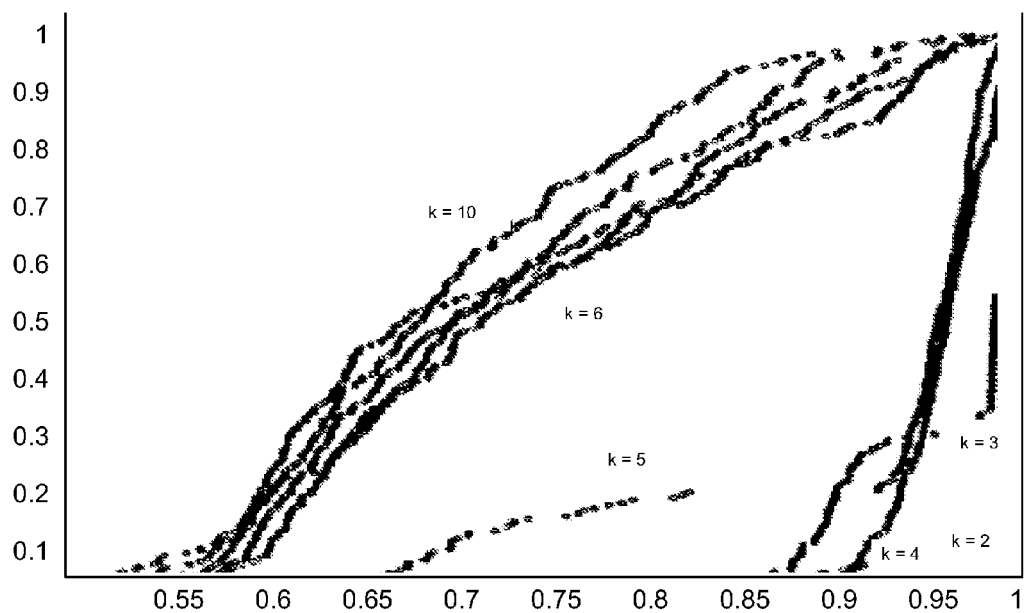

|  | Jain | Silhouette | KL | Gap | Subsamp |
|---|---|---|---|---|---|
| 4 Gauss (FIG. 1) | 4 | 4 | 9 | 4 | 4 |
| Microarray (FIG. 2) | 3 | 2 | 4 | 6 | 5 |
| Isolet (FIG. 4) | 2 | 5 | 5 | — | 3 |

In the case of clustering algorithms whose output depends on the initial condition, e.g., k-means, a distribution of scores exists even when considering a fixed sub-sample. In such cases, the method produces an indication of how varied the solutions can be for various values of k. It has been observed that for a "good" value of k, a similar transition occurs, but is generally "smeared", since k-means produces widely varying solutions. To address this, a version of k-means similar to that presented by P. Bradley and U. Fayyad in "Refining initial points for k-means clustering" (in J. Shavlik, editor, *Proc. of the 15th Inter. Conf. of Machine Learning (ICML '98)*, pages 91-99, San Francisco, Calif., 1998. Morgan Kaufmann) was used. That method produces initial conditions that converge to near optimal solutions, and use a fixed initial condition for each value of k. According to the present invention, k-means clustering produces solutions that are highly stable with respect to sub-sampling. This good result may be due to the global optimization criterion, which differs from the local bottom up approach of hierarchical clustering that appears to be less stable to sub-sampling.

Example 5

Gene Expression Data

A data set of 1600 genes with 12 time steps was utilized to illustrate the process undergone by gene expression profiles. First, the genes were ranked in order of "quality" to preselect a subset for further analysis. All the genes were ranked according to three criteria: (1) saliency (the absolute difference between their min and max value; the larger the better); (2) smoothness (a coefficient assessing the smoothness of the profile was computed; the smoother the better); and (3) reliability (the average standard deviation of the experiment replicated for the whole profile).

Figure 5A:
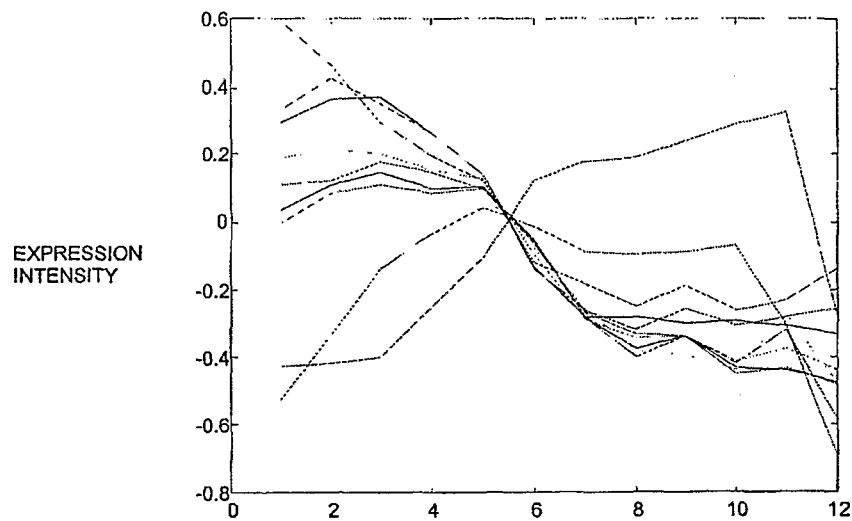
FIGS. 5a-5b are graphic representations of gene pre-selection.
Figure 5B:
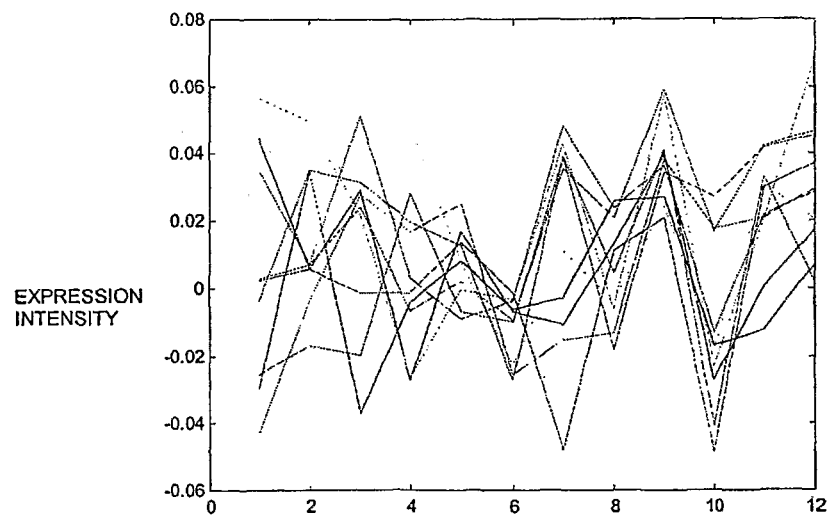

The ranks of the genes according to these three criteria were then added to form a combined criterion according to which the genes were ranked again. The result can be seen in FIGS. 5a and 5b, which show gene expression temporal profiles. The ten best genes are depicted in FIG. 5a, while the ten worst genes are shown in FIG. 5b according to a combined criterion of saliency, smoothness, and reliability.

The 5% top quality genes according to the above defined combined criterion (800 genes) were selected. A kernel clustering algorithm based on k-means was then run on random subsets of 100 genes among these 800 genes. A maximum number of clusters of ten were used, but only five did not degenerate. The stability of the solutions was verified by running again kernel k-means on the resulting cluster centers. The solution was robust with respect to increasing the number of genes (doubling, to 1600 genes), changing the subset size (to 200 genes) and the maximum number of cluster (to 20 genes).

Figure 6A:
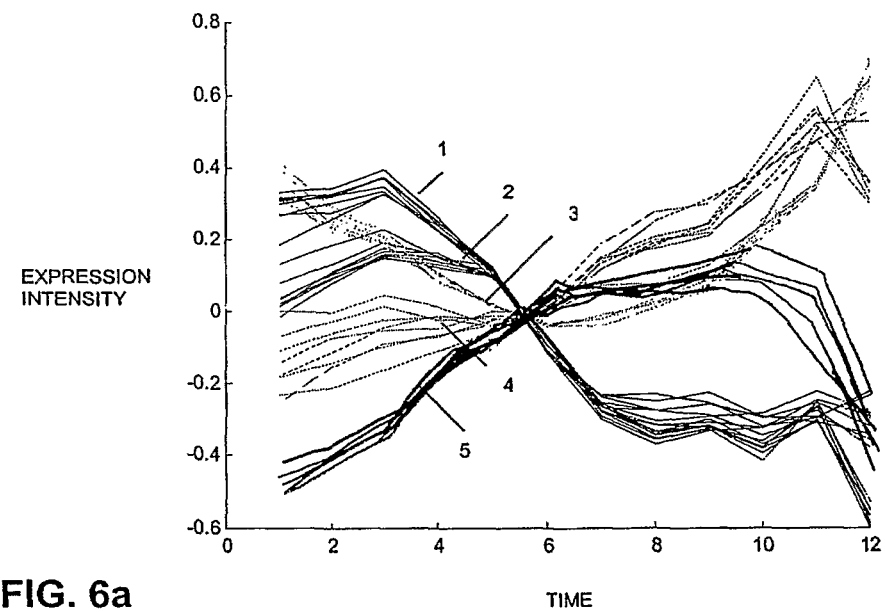
FIGS. 6a-6b are graphs of the average profiles of the clusters of the eight clustering runs and their grouping into meta-clusters.
Figure 6B:
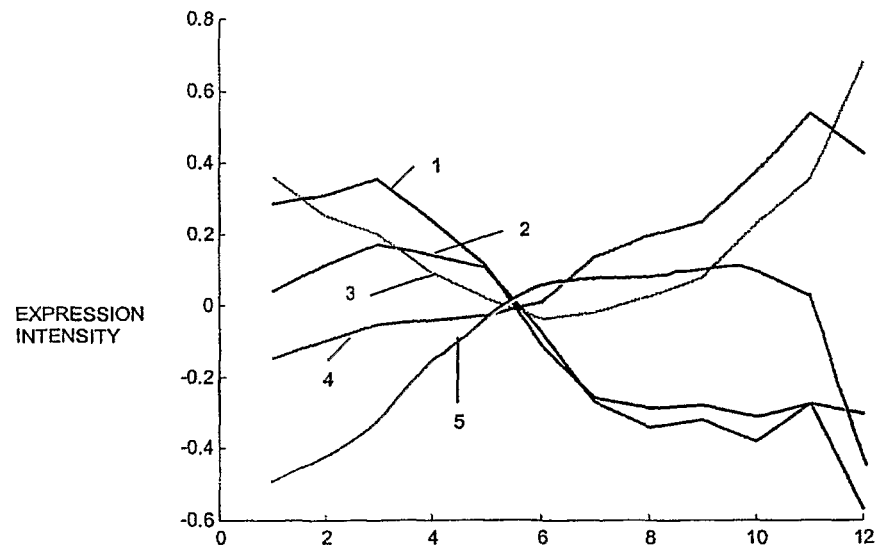

FIGS. 6a and 6b illustrate the average profiles of the clusters of the eight clustering runs and their groupings into meta-clusters 1-5. The cluster centers in FIG. 6a were obtained with multiple runs of k-means using random subsets of 100 genes in the top 800 best quality genes. FIG. 6b shows the average cluster centers for the five clusters. Only a subset of the nine possible profiles that could occur are represented.

According to the present invention, the clustering algorithm is based on, but is a variation of, the classical k-means algorithm. The algorithm operates by the following routine:

---

Initialize: Start with a random assignment of class labels to the patterns.
  Step 1: Compute cluster centers by averaging class members in each class.
  Step 2: Re-assign patterns to the cluster with nearest cluster center.
  Iterate step 1 and 2 until the assignment of patterns to classes remains constant.

---

Figure 7A:
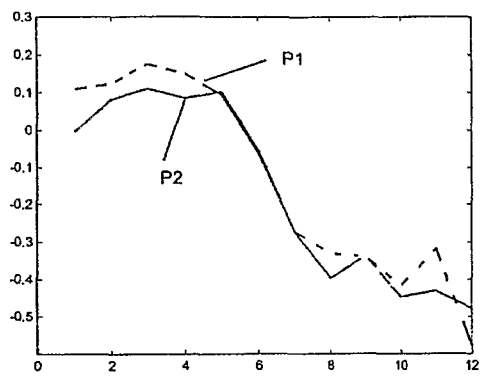
FIGS. 7a-7d are graphs of curve fitting with affine transformations.
Figure 7B:
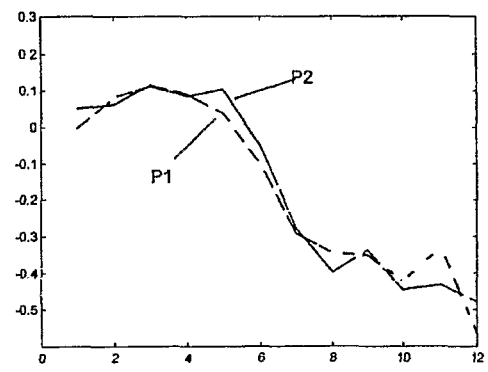
Figure 7C:
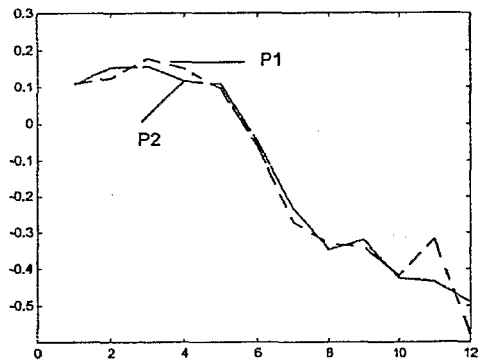
Figure 7D:
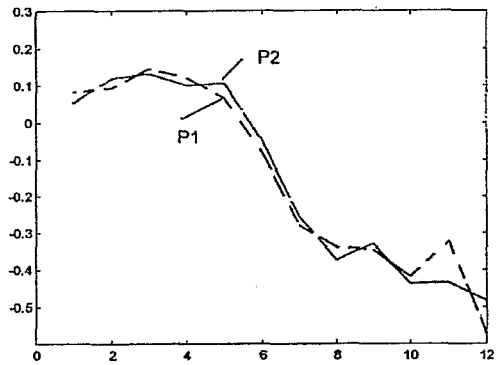

This algorithm differs from the classical k-means in that it uses a special metric to measure proximity in step 2. It is based on the residuals of a fit of one profile onto another, using an affine transformation that is a combination of translation, scaling, and rotation (to first order). Such fit is remarkably simple to implement with a couple of lines of Matlab® (The MathWorks, Inc., Natick, Mass.) and is quite fast. For example, to fit a profile (a 12 dimensional vector x2) that goes through zero between time step 5 and 6, onto another vector x1, one can write:

xx2=[x2,ones(12,1),[−5;−4;−3;−2;−1;1;2;3;4;5;6;7]];

w=xx2\x1;

x2fit=xx2*w;

residual=mean((x1-x2fit).^2);

FIGS. 7a-d depict two profiles and variations on how they can be fit one onto the other or both on their average. This provides an illustration of curve fitting with affine transformations. FIG. 7a shows the two original profiles P1 and P2. FIG. 7b shows the profile P1 fitted on P2. FIG. 7c shows profile P2 fitted on P1. FIG. 7d shows both profiles fitted to their average.

After some experimentation, the following measure of dissimilarity was adopted:

residual0+max(residual1,residual2), where residual0 is the squared Euclidean distance between x1 and x2, residual1 is the residual of the fit of x1 onto x2, and residual2 is the residual of the fit of x2 onto x1. The rationale behind this choice is that a dissimilarity simply based on the symmetric fit to the average is, in some cases, too optimistic—it becomes very easy with the type of affine transformations that are being allowed to fit any curve to a straight line (but not vice versa). Residual 0 is added to avoid allowing too large transformations. The same desirable properties could be achieved by solving an optimization problem under constraints to limit the range of transformations, but this would be computationally more expensive.

Any positive monotonic transformation of the dissimilarity does not affect the algorithm. It should also be noted that in Step 1 of the algorithm, a simple average of the patterns is used, as opposed to an average of the curves fitted to the cluster centers. After iterating, there is a significant distortion of the cluster center profiles, some of which just become straight lines.

Figure 8A:
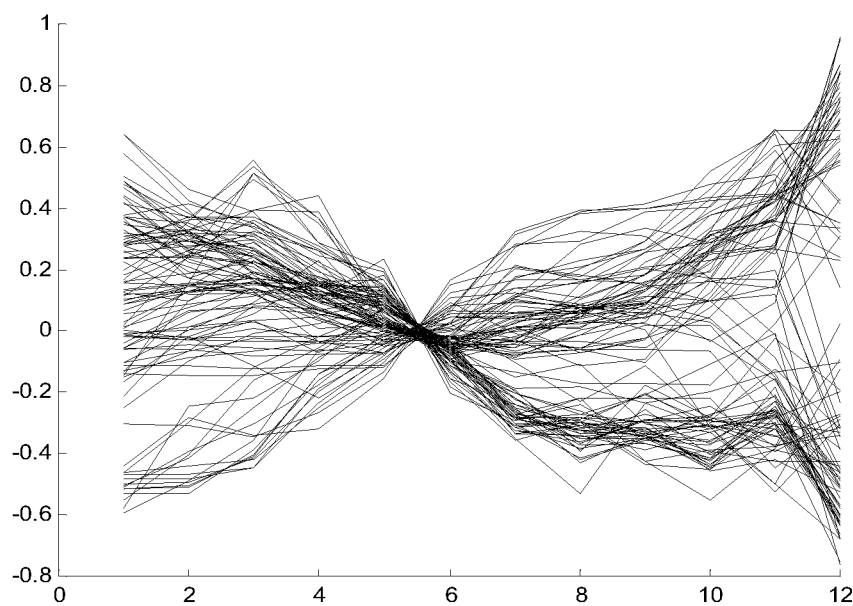
FIGS. 8a-8h are graphs of curve fitting with affine transformations, clustering obtained from the top 800 best quality genes.
Figure 8B:
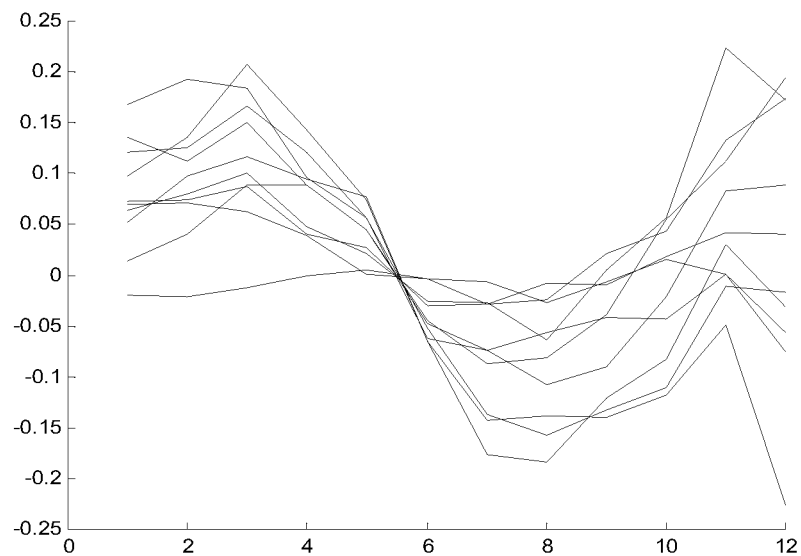
Figure 8C:
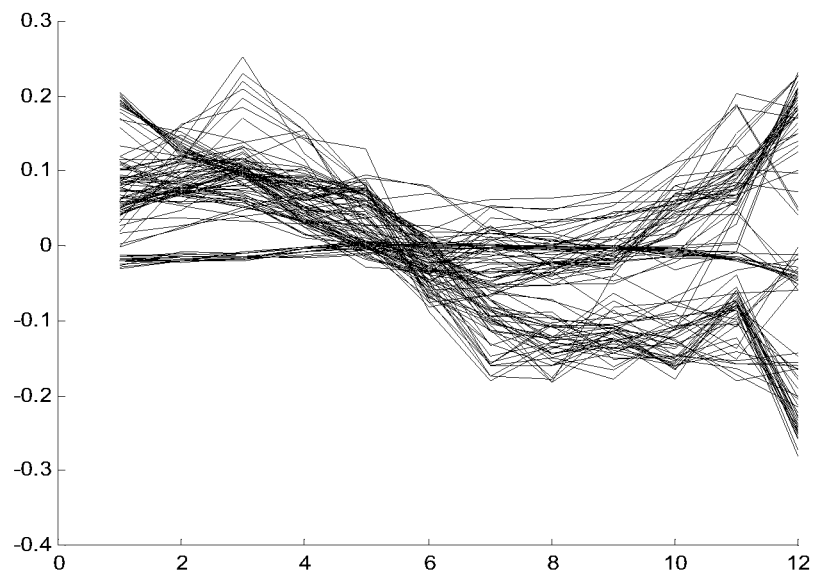
Figure 8D:
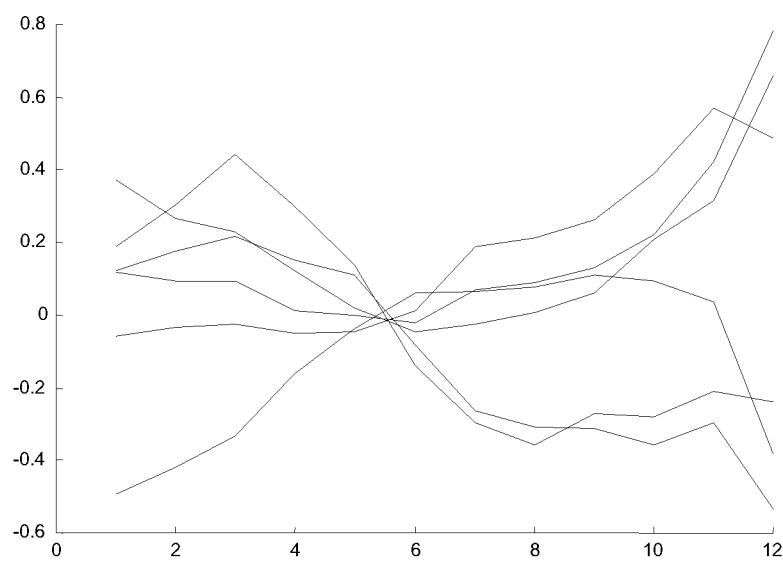
Figure 8E:
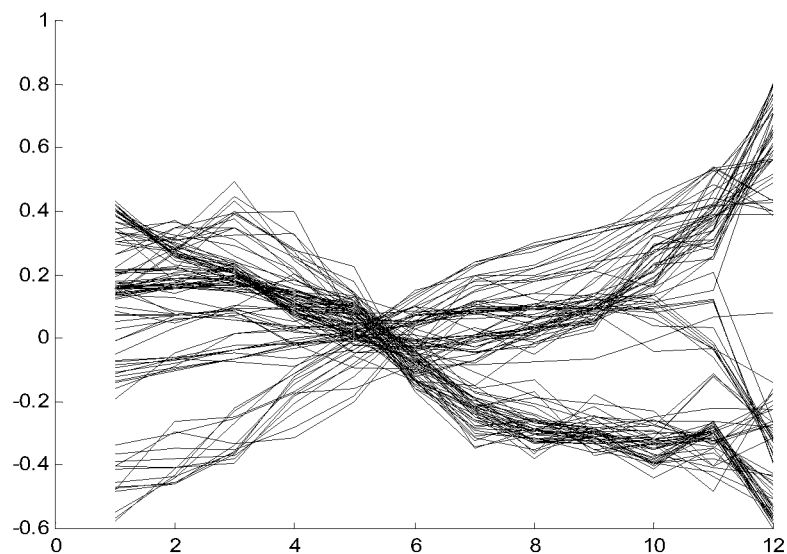
Figure 8F:
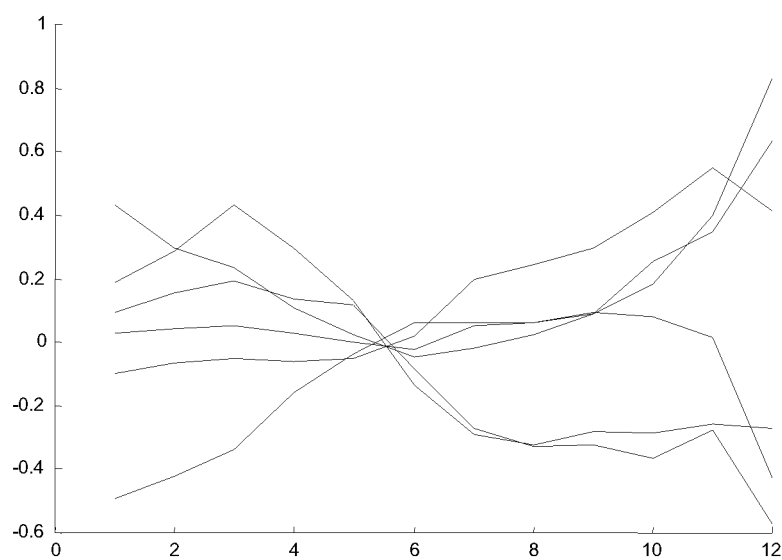
Figure 8G:
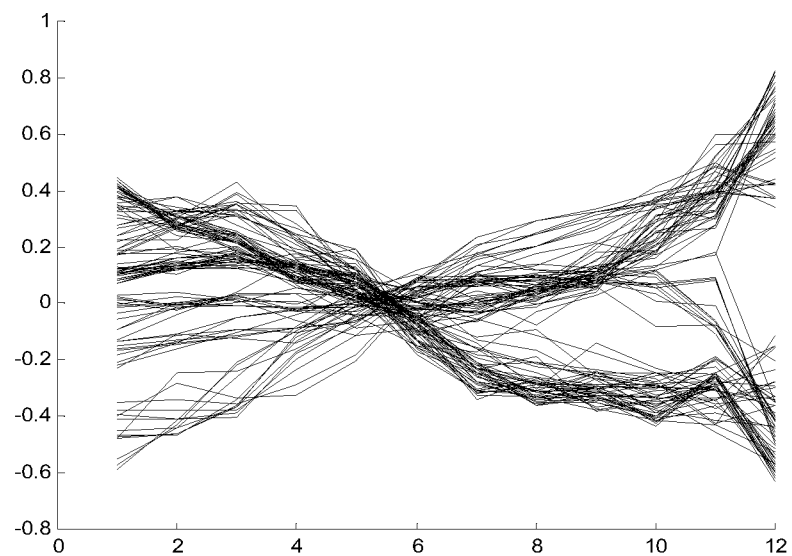
Figure 8H:
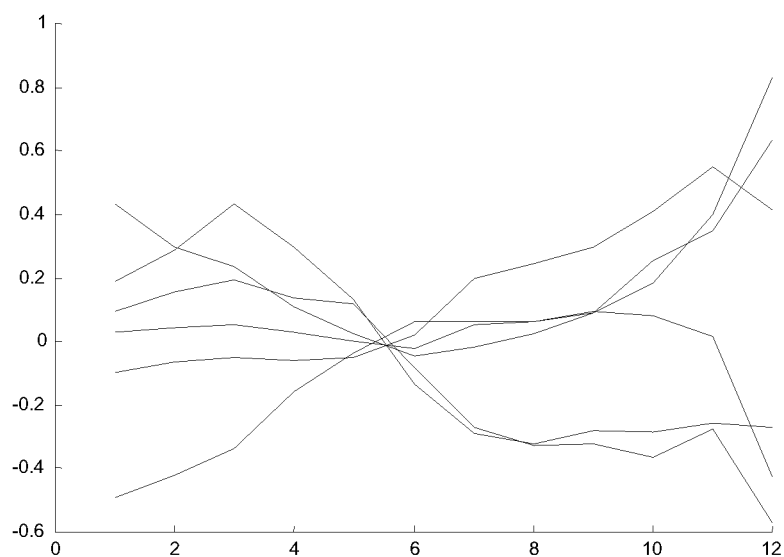

FIGS. 8a-h illustrate the results of one run of the algorithm on a subset of 100 gene expression profiles with a maximum cluster number of 10, where expression intensity is plotted with time. The clustering is obtained from the top 800 best quality genes. FIG. 8a shows the original profiles with random class label assignments. FIGS. 8c, 8e and 8g illustrate fitted profiles of cluster members at successive iterations. FIGS. 8b, 8d, 8f, and 8h show the cluster centers at successive iterations.

The present invention provides a method for model selection in clustering. Most other approaches in the prior art are based on either the sum squared distances within clusters, or some combination of within-cluster distances and between-cluster distances. Not only do these prior art methods impose the notion of how a cluster should look (e.g., "compact"), most of the methods performed poorly in practice. The inventive method, on the other hand, provides a description of the stability of a clustering method with respect to re-sampling or noise. It is believed that this stability captures the notion of "inherent" structure that is the goal in the validating clustering solutions.

Another advantage of present invention is that it is useful in identifying the absence of structure in the data. This differs from most clustering validation algorithms of the prior art, with the exception of the gap statistic, which can only determine the number of clusters if that number is larger than 1.

The invention claimed is:

1. A computer implemented method for identifying co-regulation patterns within gene expression data comprising gene expression levels, the method comprising:

(a) inputting the data into a computer system having a memory and a processor for executing a clustering algorithm;

(b) selecting a clustering algorithm based on a dissimilarity measure between pairs of principal components of the gene expression levels;

(c) randomly assigning class labels to the gene expression levels;

(d) defining a plurality of clusters of gene expression levels within each labeled class;

(e) measuring dissimilarity between each cluster of gene expression levels by measuring a residual of a fit of one cluster onto another cluster, wherein the residual fit comprises using a fit that is invariant with respect to affine transformations, wherein the affine transformations comprise a combination of translation, scaling and rotation;

(f) reassigning gene expression levels to the labeled class with the most similar cluster;

(g) repeating steps (d) through (f) until assignment of gene expression levels to the labeled classes remains constant; and (h) displaying a graph showing the gene expression levels clustered into the labeled classes, wherein the labeled classes correspond to co-regulation activity.

2. The method of claim 1, wherein the clustering algorithm is a k-means algorithm.

3. The method of claim 1, further comprising, prior to step (b), ranking the gene expression data according to one or more quality criteria and using a pre-determined fraction of top ranked gene expression data for steps (b) through (g).

4. The method of claim 3, wherein the one or more quality criteria are selected from saliency, smoothness and reliability.

5. The method of claim 1, wherein the gene expression levels comprise mRNA expression levels measured on a microarray.

6. The method of claim 1, wherein the gene expression levels are measured at different time steps.

7. A computer implemented method for identifying co-regulation patterns within a dataset comprising gene expression levels, the method comprising:

inputting the dataset into a computer system having a memory and a processor for executing a clustering algorithm;

selecting a plurality of granularity levels k, and for each granularity level k:
  (a) inducing perturbations in the dataset to generate a modified dataset;
  (b) applying the clustering algorithm to the at least one modified dataset to produce k clusters under each of the perturbations;
  (c) creating a data subset comprising the clusters identified in step (b);
  (d) applying the clustering algorithm to the data subset using the same value of k clusters;
  (e) determining the stability of the clusterings at each granularity level k by measuring dissimilarity between data in the data subset and the cluster center for the cluster into which the data was assigned;

measuring fit of the data to the cluster centers for all k granularity levels, wherein the fit comprises using a fit that is invariant with respect to affine transformations, wherein the affine transformations comprise a combination of translation, scaling and rotation;

selecting from among the plurality of granularity levels an optimum granularity level k corresponding to the best fit;

generating an output comprising the dataset clustered into a plurality of subsets corresponding to the optimal granularity level k; and displaying a graph showing the gene expression levels clustered into the plurality of subsets, wherein the subsets correspond to co-regulation activity.

8. The method of claim 7, wherein the perturbations comprise a combination of one or more of sub-sampling the dataset, changing initialization of the clustering algorithm, and adding noise to the dataset.

9. The method of claim 7, further comprising, prior to selecting a plurality of granularity levels, ranking the gene expression data according to one or more quality criteria and selecting a pre-determined fraction of top ranked gene expression data.

10. The method of claim 9, wherein the one or more quality criteria are selected from saliency, smoothness and reliability.

11. The method of claim 7, wherein the gene expression levels comprise mRNA expression levels measured on a microarray.

12. The method of claim 7, wherein the gene expression levels are measured at different time steps.

13. A computer implemented method for determining co-regulation patterns within a gene expression dataset comprising gene expression levels, the method comprising:

inputting the dataset into a computer system having a memory and a processor for executing a clustering algorithm;

randomly assigning labels to the gene expression levels in the dataset by partitioning the dataset into k subsets, wherein k has a minimum number and a maximum number;

for each value of k, beginning with the minimum value, for each pair of subsets, computing a correlation score on the intersection between the pair of subsets, wherein the correlation score comprises a similarity measure between the pair of subsets and the greatest similarity has the highest score; and displaying a histogram comprising a distribution of the correlation scores for each value of k, wherein the distribution comprising the highest value of k that remains concentrated near the highest correlation score corresponds to a clustering of the gene expression levels according to co-regulation activity.

14. The method of claim 13, wherein the step of computing the correlation score comprises selecting a fraction of the gene expression levels in each subset for comparison with other subsets.

15. The method of claim 14, wherein the fraction is greater than 0.5.

16. The method of claim 13, further comprising, prior to randomly assigning labels, ranking the gene expression data according to one or more quality criteria and selecting a pre-determined fraction of top ranked gene expression data.

17. The method of claim 16, wherein the one or more quality criteria are selected from saliency, smoothness and reliability.

18. The method of claim 13, wherein the gene expression levels comprise mRNA expression levels measured on a microarray.

19. The method of claim 13, wherein the gene expression levels are measured at different time steps.

20. A computer implemented method for identifying co-regulation patterns within a gene expression dataset comprising gene expression levels, the method comprising:

inputting the dataset into a computer system having a memory and a processor for executing a clustering algorithm;

randomly assigning labels to the gene expression levels in the dataset by partitioning the dataset into k subsamples, wherein k has a minimum number and a maximum number;

representing each subsample by a matrix;

computing a dot product between pairs of subsamples to generate a correlation score on an intersection between the pair of subsamples, wherein the correlation score comprises a similarity measure between the pair of subsamples and the greatest similarity has the highest score; and generating a display comprising a distribution of the correlation scores for each value of k, wherein the distribution comprising the highest value of k that remains concentrated near the highest correlation score corresponds to a clustering of the gene expression levels according to co-regulation activity.

21. The method of claim 20, further comprising, prior to randomly assigning labels, ranking the gene expression data according to one or more quality criteria and using a predetermined fraction of top ranked gene expression data for subsequent steps.

22. The method of claim 21, wherein the one or more quality criteria are selected from saliency, smoothness and reliability.

23. The method of claim 20, wherein the gene expression levels comprise mRNA expression levels measured on a microarray.

24. The method of claim 20, wherein the gene expression levels are measured at different time steps.

* * * * *